United States Patent
Ross et al.

(10) Patent No.: US 7,799,520 B2
(45) Date of Patent: Sep. 21, 2010

(54) DEVICES AND METHODS FOR ISOLATING AND RECOVERING TARGET CELLS

(76) Inventors: Amelia A. Ross, 23952 Dory Dr., Laguna Niguel, CA (US) 92677; Steve Bernstein, P.O. Box 838, Los Olivos, CA (US) 93441

( * ) Notice: Subject to any disclaimer, the term of this patent is extended or adjusted under 35 U.S.C. 154(b) by 0 days.

(21) Appl. No.: 11/744,130

(22) Filed: May 3, 2007

(65) Prior Publication Data

US 2007/0202530 A1      Aug. 30, 2007

Related U.S. Application Data

(63) Continuation of application No. 10/247,223, filed on Sep. 18, 2002, now abandoned.

(60) Provisional application No. 60/364,679, filed on Mar. 15, 2002.

(51) Int. Cl.
*C12Q 1/00* (2006.01)

(52) U.S. Cl. ............................ 435/4; 435/40.5; 435/41

(58) Field of Classification Search ........................ None
See application file for complete search history.

(56) References Cited

U.S. PATENT DOCUMENTS 6,673,620 B1 *   1/2004   Loeffler et al. ................ 436/46

* cited by examiner

*Primary Examiner*—Jacob Cheu
(74) *Attorney, Agent, or Firm*—Inskeep IP Group, Inc.

(57) ABSTRACT

A cell isolating device and method is provided to concentrate or isolate cells with specific characteristics from a mixture of different cell types. One embodiment may comprise two sub-types of antibodies that are directly conjugated to biotin ($Ab_b$) and conjugated to a fluorescent molecule ($Ab_f$). The conjugated antibodies ($Ab_b$+$Ab_f$) bind to the target cells in a mixed cell suspension. The cell suspension is then passed over an immobilized avidin or streptavidin substrate on a glass microscope slide. The biotinylated target cells adhere to the avidin/streptavidin substrate, while the unbound cells are washed off and collected in a wicking member. Captured cells on the avidin/streptavidin substrate may then be visualized directly using a fluorescent microscope or detected and enumerated via an on-board fluorescent detection device. Additional chemicals and/or physical manipulation may then be applied to the device to release viable target cells for subsequent analysis.

27 Claims, 3 Drawing Sheets

DEVICES AND METHODS FOR ISOLATING AND RECOVERING TARGET CELLS

CROSS REFERENCE TO RELATED APPLICATIONS

The present invention is a continuation of U.S. patent application Ser. No. 10/247,223 filed Sep. 18, 2002, now abandoned which claims benefit of U.S. Provisional Application Ser. No. 60/364,679, filed Mar. 15, 2002; both of which are incorporated herein by reference.

BACKGROUND OF THE INVENTION

All living bodies are comprised of individual cells, each cell defining an environment where various biological and chemical reactions take place. In particular, each cell contains a cell membrane that separates the internal environment of the cell from the external environment and thereby controls the entry and exit of various nutrients and waste. Additionally, the cell membrane includes various proteins, sugars, and other molecules that "identify" a particular cell type, these identifying molecules commonly being referred to as antigens.

In order to better understand the function and pathologies of cells, numerous methods have been developed to isolate and concentrate a desired target cell population from a mixed cell population so that the target cell population can be further analyzed. One such method is based upon cell density wherein a mixture of cells is spun at high speeds in a centrifuge so that the higher density cells become separated for the lesser density cells. Although this method is effective at separating different cells, centrifugation does not have good cell-separation specificity as different types of cells may have the same or similar cell density.

Accordingly, more sophisticated cell separation techniques have been developed wherein cells are separated based upon the presence of certain cellular identifiers, namely, antigens, found on the cellular membrane. More specifically, these selection methods are based upon using antibodies that react with antigens found on a particular target cell membrane. In one such method, the antibodies are affixed on the surface of a substrate, such as magnetic beads or small iron-coated particles. When mixed with the cell sample, the antibody-coated beads or particles bind to the specific antigens on the cell membrane. As a sample cell solution is passed through a magnetic separation column, the magnetic particles with the target cells attached then bind to the surface of the magnetic field. The target cells are then released from the column by removing the magnetic field from the cell separation column. Other known methods use variations of target cell binding in continuous-flow "immunoaffinity" columns. Generally, with immunoaffinity columns, once the target cells bind to the column by antigen-antibody affinity, the bound target cells are released by mechanically agitating the immunoaffinity column.

Cell separation techniques based upon cellular membrane identifiers are particularly useful in isolating specific cells as such techniques may be modified or tailored for specific target cells. Indeed, such highly specific cell separation techniques are particularly useful for diagnosing and treating specific and potent diseases such as, but not limited to, autoimmune diseases or cancer.

The utility of immunoseparation techniques as a diagnostic tool is evident given the prevalence of various diseases. Cancer, for instance, is expected to afflict approximately 1.3 million people in 2002 and result in approximately 500,000 deaths. Studies have shown, however, that early detection of cancer results in improved survival rates as treatment is more likely to be successful during the early stages of cancer. Yet while early diagnosis and treatment increases the chances of survival, there still remains the possibility of relapse. Accordingly, there has been considerable research into the causes of cancer relapse.

In particular, over the past 12 years, numerous research studies have been designed to track the presence of low numbers of micrometastic tumor cells (so called "micrometastases") in blood, bone marrow, and effusion fluids in patients with cancer. Studies have shown that the presence of tumor micrometastases in blood and bone marrow at time of surgery is a strong prognostic indicator of poor prognosis and early relapse in breast, prostate, ovarian, and lung cancer patients. Furthermore, the reappearance of circulating tumor cells following chemotherapy appears to herald the earliest indication of disease recurrence. Accordingly, the early detection of these micrometastases may result in higher survival rates for patients in relapse.

While the presence of micrometastases are strong indicators of cancer, these tumor cells are particularly difficult to detect as the reported frequency of micrometastatic tumor cells range from 1-5 micrometastatic tumor cells per 100,000-1,000,000 bone marrow cells and from 1 micrometastatic tumor cell in 1,000,000 to 100,000,000 blood cells. Despite the low frequency of micrometastases, various methods have been developed to concentrate or isolate the micrometastatic cells from blood, bone marrow, or effusion fluids using immunoselection methods such as, but not limited to, immunomagnetic separation/isolation, immunocolloidal separation/isolation, or flow cytometric separation/isolation.

While these prior art immunoselection methods have proven useful, these methods can be inefficient as they require considerable operator intervention during the separation process. For instance, the separation column usually needs cleaning and priming prior to the introduction of a sample solution. Furthermore, the column requires constant monitoring during the separation process. As a result, the efficiency, accuracy, and recovery of targeted cell is often directly related to operator skill or error. Accordingly, it is desirable to have a cell separation device that minimizes operator error.

Moreover, the design of prior art immunoseparation columns may also hinder the recovery of a targeted cell. For instance, immunomagnetic separation/isolation methods result in permanent or semi-permanent adherence of magnetic beads/particles to the isolated cells. Accordingly, the difficulty and sometimes inability to remove the target cells from the magnetic beads reduces the accuracy of these methods. For example, isolated target cells may become damaged when the cells are separated from the column as relatively harsh chemical or mechanical processes are typically required to remove the target cells from the beads. This is particularly problematic when attempting to detect cells, such as micrometastases, which have a low frequency.

Furthermore, target cell recovery is predicated on having the proper target cell to magnetic bead ratio. If the target cell to bead ratio is not properly optimized, "background" interference may develop due to the presence of beads or particles that are not bound to the target cells thereby reducing the method's accuracy. However, optimizing the target cell to bead ratio is difficult as the frequency of the target cell is usually unknown.

Accordingly, there remains a need for devices and methods that optimize target cell isolation, purity, and viability. There also remains a need for devices and methods that isolate viable, uncompromised cells (physically and/or biochemically) so as to enable subsequent analysis and potential therapeutic applications of the isolated cells.

BRIEF SUMMARY OF THE INVENTION

The present invention relates to a device and method of concentrating or isolating a target cell from a mixture having different cell types. More specifically, the target cells are isolated onto a fixed substrate through the use of a bifunctional molecule wherein a first functional group of the molecule is reactive with the fixed substrate and the second functional group is reactive with the target cell. That is, target cells may be more easily recovered and identified because the steps of isolation and identification are carried out on the same substrate. In contrast, prior art devices and methods typically require two or more substrates to isolate and identify the target cell. In an exemplary embodiment, the present invention may be utilized in the detection of rare cellular events (e.g., tumor cells in blood, bone marrow, effusion fluids, virally infected cells, cells carrying aberrant genetic information).

According to an exemplary embodiment, the cell separating device comprises a substantially planar surface having a bioactive coating applied thereon and at least one bifunctional compound capable of binding to said target cell and to said bioactive coating. The bifunctional compound allows for the isolation of the target cell from a cellular mixture.

According to another exemplary embodiment, the cell separating device comprises a substantially planar surface having a bioactive coating applied thereon. The device further includes a conduit in spaced relationship with the planar surface, wherein the conduit includes at least one channel to deliver a cellular mixture to the bioactive coating. The device also includes a fluid absorbing media provided on the planar surface and positioned adjacent to the bioactive coating.

The present invention also provides methods of isolating a target cell from a cellular mixture. According to the teachings of the present invention, the method comprises the steps of providing a cell separation device having a planar surface coated with a bioactive coating and a bifunctional compound. The bifunctional compound is combined with the cellular mixture, and this mixture is then exposed to the bioactive coating. The bioactive coating is then analyzed for the presence of the target cell.

DETAILED DESCRIPTION OF THE INVENTION

Figure 1:
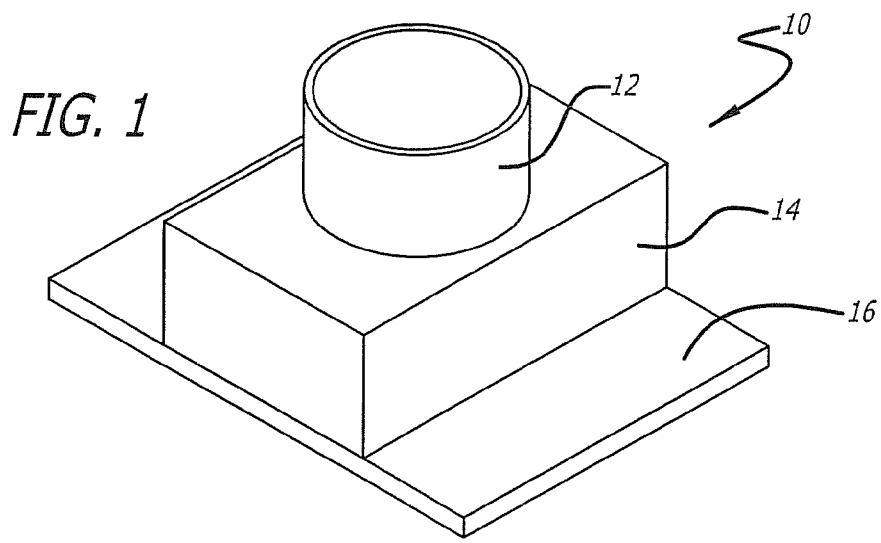
FIG. 1 is a perspective of the cell separation device made in accordance with the teachings of the present invention.

The present invention relates to devices and methods of isolating and identifying a desired target cell on a single substrate. More specifically, the desired target cell is isolated from the various cells by targeting the various antigens found on the cell membrane of the target cell. That is, the present invention utilizes monoclonal antibodies that are directly conjugated to biotin and to a marker molecule wherein the conjugated antibodies are designed to bind to particular antigens found on the target cells. The present invention also utilizes the unique binding affinity of biotin (or biotin derivatives) to avidin or streptavidin to isolate the desired target cell from the cellular mixture. The target cells are separated from the cell suspension when the cell suspension is passed over an immobilized avidin or streptavidin substrate. As a result, the conjugated cells adhere to the avidin/streptavidin substrate, while the unbound cells are washed off and collected in a wicking member. The captured cells can then be reacted with other antibodies for subsequent detection and enumeration. Furthermore, the methods of the present invention allows for release of the target cells by chemical and/or mechanical methods.

The device and methods are advantageous over the prior art cell separation devices. First, the present invention optimizes target cell recovery and purity as the captured target cell may be easily identified and separated from the substrate. Rather, unlike prior art devices that utilize spherical beads, the present invention utilizes a planar substrate where the target cell may be separated from a cell mixture and may also be identified on the substrate. Consequently, the isolated cells may easily be identified on a planar surface as compared to a spherical bead. Moreover, the present invention also eliminates the steps of removing the target cell from the substrate for subsequent identification. Rapid identification and capture of a specific target cell is particularly important where the target cell, such as micrometastases, has a very low frequency. Nevertheless, the devices and methods of the present invention are also useful for identifying and capturing target cells that have a lower or greater frequency than micrometastases.

Moreover, the target cells captured with the cell separation device of the present invention are uncompromised physically or biochemically. Accordingly, the captured cells may be more easily recovered and analyzed as compared to prior art techniques. Unlike the prior art techniques, the isolated target cells of the present invention are not directly bound to the substrate. Rather, the isolated target cell is separated from a cell mixture by utilizing the binding affinity of avidin and biotin. Consequently, the isolated target cells are more easily separated from the substrate than is possible with target cell removal from spherical beads or magnetic particles. Additionally, the device of the present invention is more efficient as compared to prior art devices and limits operator error. That is, according to the present invention, the target cell may be isolated, identified, and subsequently released from the same fixed substrate.

Figure 2:
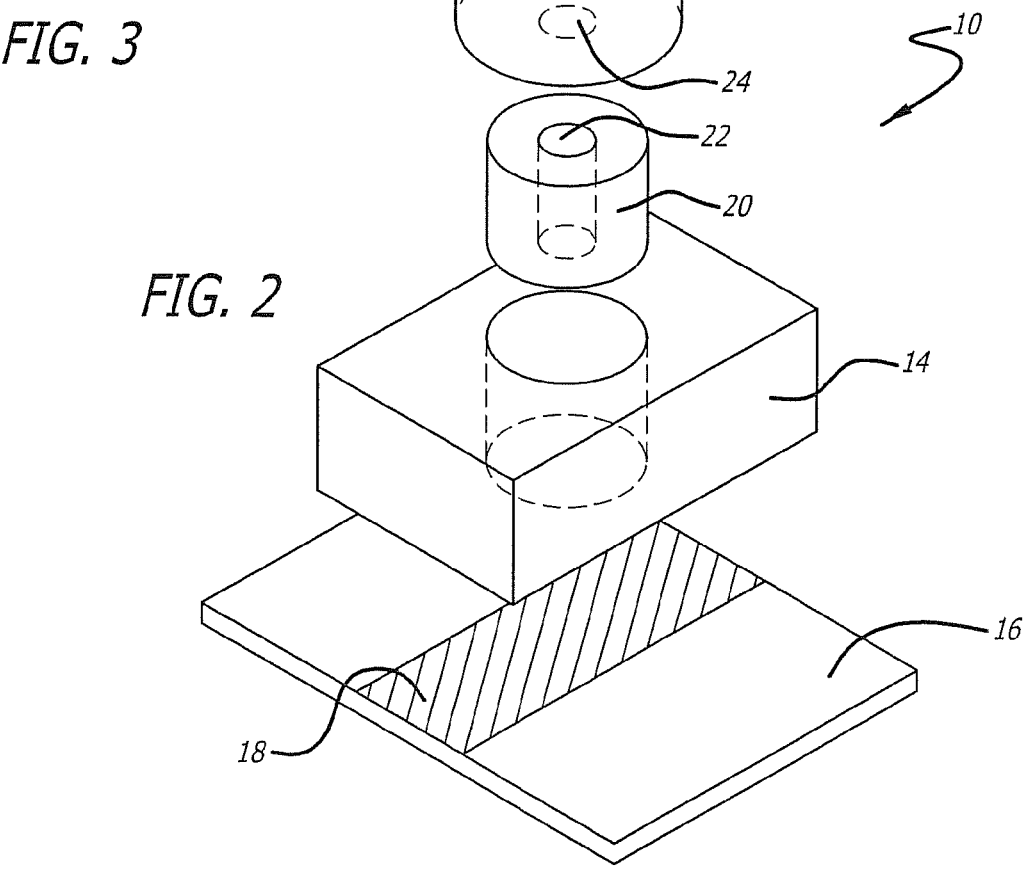
FIG. 2 is an exploded perspective view of FIG. 1.

According to an exemplary embodiment of the present invention, the cell separation apparatus 10 comprises a fixed substrate 16 such as, but not limited to, a standard glass microscope slide. The fixed substrate 16 may be made from materials such as, but not limited to, metal, glass, plastic, or ceramic materials. As shown in FIG. 2, the fixed substrate 16 is provided with a bioactive coating 18 applied to a defined area that may have a plurality of shapes such as, but not limited to, a circle, an oval, a square, or a rectangle. According to exemplary embodiments of the present invention, the bioactive coating 18 may be avidin, streptavidin, or derivatives thereof. For purposes of example, but not of limitation, the bioactive coatings will be referred to as "avidin" coating.

The avidin coating 18 may be applied to the fixed substrate 16 by a number of methods. One method includes directly bonding avidin 18 to the fixed substrate's surface. By directly attaching the avidin to the fixed substrate 16, covalent chemical bonding techniques are required. Generally, the fixed substrate 16 must possess chemical functional groups on its surface such as carbonyl groups, primary amines, hydroxyl groups, silane groups which will form a strong, chemical bond with similar groups on the active compound. In the absence of such chemical forming functional group, techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, and etching with strong organic solvents.

According to an alternative method, avidin 18 is indirectly bound to the fixed substrate's surface 16 through an intermediate layer (not shown). This intermediate layer may be either covalently bound to the fixed substrate's surface or bonded through strong intermolecular attractions such as ionic or Van der Waals forces. Examples of commonly used intermediate layers include, but are not limited to, organic polymers such as silicones, polyamines, polystyrene, polyurethane, acrylates, and methoxysilanes.

Figure 3:
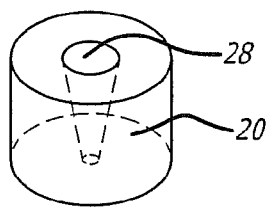
FIG. 3 is a perspective view of an alternate embodiment of the capillary annulus.

As shown in FIG. 2, the capillary annulus 20 is a generally cylindrical structure having a conduit 22 that extends along the longitudinal axis of the cylindrical structure through which the cell sample may travel. The capillary annulus 20 may be made from a number of different materials such as, but not limited to, plastic, metal, or ceramic. In an alternate embodiment, the capillary annulus 20 may include a plurality of conduits that extend along the longitudinal axis. As shown in FIG. 1, the conduit 22 has a constant diameter along the length of the conduit. In an alternate embodiment, the conduit 28 may be tapered (conical) or have a decreasing radius as illustrated in FIG. 3.

The capillary annulus 20 is placed in spaced communication with the fixed substrate 16. The distance between the base of the annulus and the fixed substrate 16 is a factor in defining the flow rate of the cell sample across the avidin coated portion 18 of the fixed substrate 16. This distance is also related to the binding efficiency between the biotinlyated antibodies and the avidin as the binding efficiency is predicated on the contact time between the biotinlyated antibodies and the avidin coating. In a preferred embodiment, this distance is in the range of 2 to 20 microns.

Optionally, the capillary annulus 20 may be provided with at least one protuberance (not shown) extending axially from the edge of the base of the annulus. The protuberance(s) may be positioned along the perimeter of the annulus and is sized so that the annulus 20 is consistently spaced a specified distance from the avidin coated area 18 of the fixed substrate. As those skilled in the art will appreciate, the protuberances may be sized differently to effect different distances between the base of the capillary annulus 20 and the surface of the fixed substrate 16. Furthermore, the capillary annulus 20 may include at least one fastening member such as, but not limited to, braces, latches, clamps, or hooks (not shown) provided about the periphery of the annulus. The fastening members serve to secure the annulus 20 to the fixed substrate 16. The fastening members are shaped to permit the attachment and removal of the annulus 20 from the substrate 16.

The cell separation device 10 may also include a specimen chamber 12 that is in communication with the capillary annulus 20. The specimen chamber 12 is a generally cylindrical chamber having at least one opening 24 provided on the bottom surface of the chamber that corresponds to the conduit opening 22 on the capillary annulus 20. In a preferred embodiment, the specimen chamber 12 is adapted to hold approximately 5.0 mL to 25.0 mL of solution. The specimen chamber 12 may be made from materials such as plastics, metals, or ceramics. As illustrated in FIGS. 1-2, the specimen chamber 12 may be reversibly attachable and detachable from the capillary annulus 20. In an alternate embodiment, those skilled in the art will appreciate that the capillary annulus 20 and the specimen chamber 12 may be made from a single piece of material.

As shown in FIGS. 1-2, a fluid absorbing media 14 surrounds the capillary annulus 20. According to one embodiment, the fluid absorbing media 14 is reversibly attached to the fixed substrate 16 by a fastening means (not shown) such as, but not limited to, braces, latches, clamps, or hooks. According to another embodiment of the present invention, the fluid absorbing media 14 may be permanently affixed to the fixed substrate 16 with glue or other bonding agents. The fluid absorbing media 14 may be comprise absorbent materials such as, but not limited to, cellulose acetate, polyester, nylon, polyolefin, or blends thereof. According to one exemplary embodiment, the fluid absorbing media 14 comprises thermal bonded extra absorbent materials supplied by Filtrona Richmond Inc. The fluid absorbing media 14 is sized to have sufficient capacity to absorb at least a volume of cells equivalent to the maximum capacity of the specimen chamber 12. Those skilled in the art will appreciate that the size and shape of the fluid absorbing media 14 may deviate from what is depicted in FIG. 1.

The fluid absorbing media 14 absorbs the unbound cells and solution that have been exposed to avidin 18 on the fixed substrate 16. Additionally, the absorptive properties of the media 14 also contribute to the binding efficiency between the biotinylated antibodies and the avidin coating. That is, the greater the absorptive properties of the media 14, the less resulting contact time between the solution and the avidin 18. Accordingly, the absorptive efficiency of the fluid absorbing media 14 must be selected so as to optimize the time for the biotinylated antibodies to bind to the avidin coating on the substrate 16.

The cell separation device of the present invention also includes at least two types of conjugated antibodies. The antibodies may be conjugated with either a biotin molecule or a marker molecule. Moreover, the antibodies are specific for the target cells and are non-reactive with the mixed cell population such as, but not limited to, blood, bone marrow, or effusion fluids. For instance, according to one embodiment of the present invention, a pan-epithelial cell antibody may be utilized. Such antibody is directed to antigens present on epithelial cell membranes. Accordingly, the cell separation device utilizing these antibodies will target and separate those cells that have antigens that react with the pan-epithelial antibody. In an alternate embodiment, antibodies that are specific to certain blood cell antigens (known as CD antigens) may be utilized. For example, CD19 and CD20 antibodies may be used to selectively capture B lymphocytes in a mixed population of blood or bone marrow cells. In yet another embodiment, antibodies to infectious agents such as, but not limited to, cytomegalovirus or HIV may also be used to selectively capture infectious cells in blood or body fluid samples.

Additionally, the present invention includes antibodies that are conjugated with marker molecules such as, but not limited to, flurochromes, radiolabels, fluorescent agents, or chromophores. The antibodies that are conjugated with a marker molecule allow the isolated target cell to be easily identified on the avidin coated slide. Accordingly, the present invention provides a device wherein cell separation and identification may occur on the same substrate.

Furthermore, according to alternate embodiments of the present invention, binder molecules, other than an antibodies, may be conjugated with biotin. The binder molecules include, but are not limited to, glycoconjugates, lectins, hormones, cell receptors, vitamins, amino acids, sugars, lipids, fatty acids, liposomes, DNA probes, or RNA probes. These binder molecules may be utilized to target particular lectins, enzymes, receptors, transport proteins, hydrophobic sites, membranes, nucleic acids, or genes.

Figure 4:
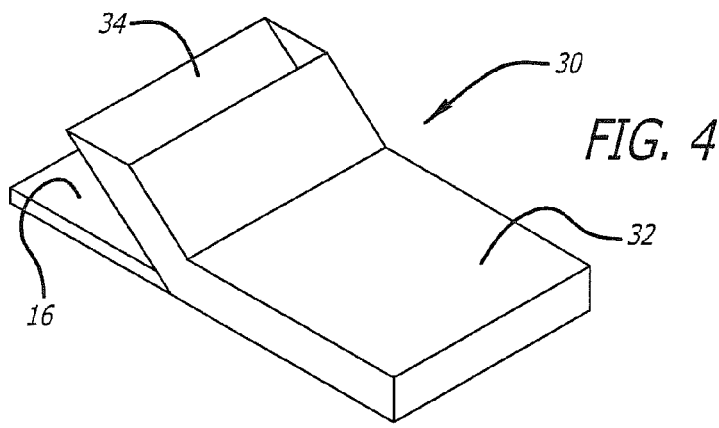
FIG. 4 is a perspective view of another exemplary embodiment of the cell separation device made in accordance with the teachings of the present invention.
Figure 5:
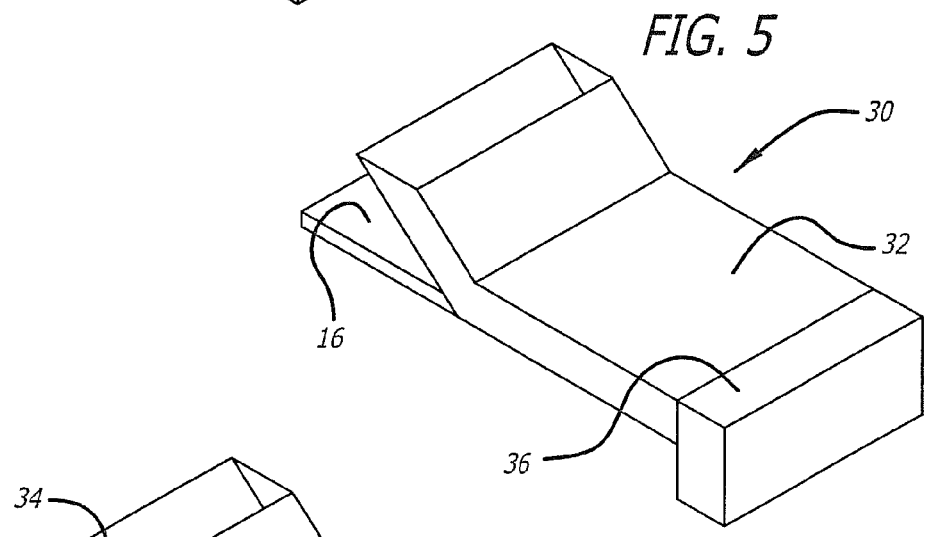
FIG. 5 is a perspective view of yet another exemplary embodiment of the cell separation device made in accordance with the teachings of the present invention.
Figure 6:
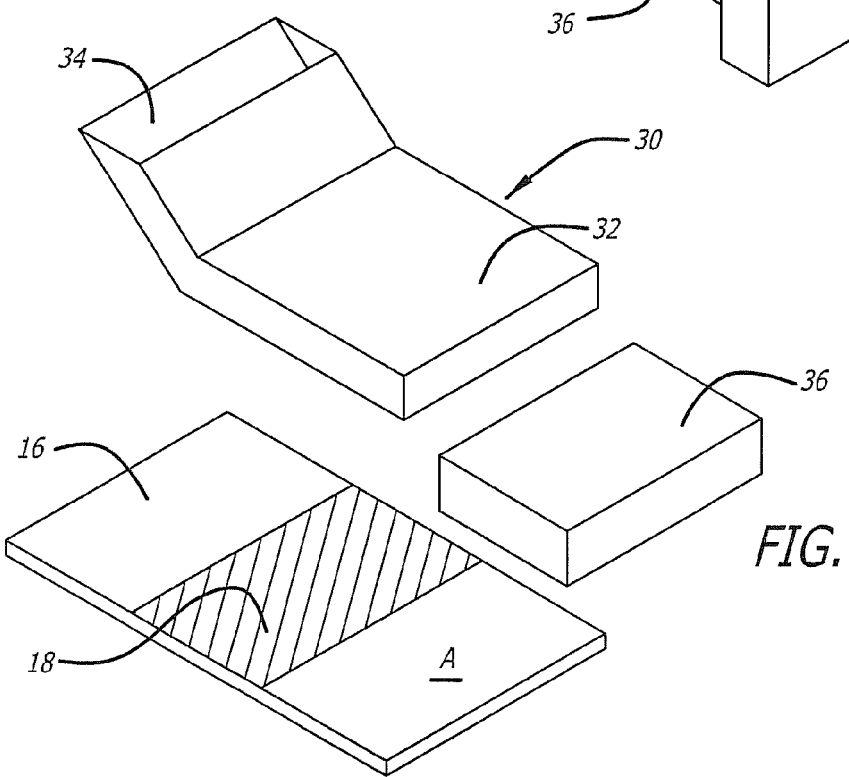
FIG. 6 is an exploded perspective view of FIG. 4.

FIGS. 4-6 illustrate other exemplary embodiments of the present invention. The cell separation device 30 comprises a fixed substrate 16 having an avidin coating 18 provided thereon, a specimen chamber 34, a capillary flow chamber 32 and a fluid absorbing media 36. Like the previous embodiment of the present invention, the avidin is provided on a defined area of the fixed substrate 16. The capillary flow chamber 32 is in communication with the fixed substrate 16 and spans at least the avidin coated region 18 of the fixed substrate 16. The capillary chamber 32 is a housing having a top wall, a first side wall, and a second side wall. The top wall is configured such that the top wall is approximately parallel to the surface of the fixed substrate 16. The first and second side walls span between the top wall and the surface of the fixed substrate 16 to define a conduit. The side walls are configured such that the capillary flow chamber 32 is reversibly attached to the fixed substrate 16 by a fastening means (not shown). The fastening means may be fasteners such as, but not limited to, braces, latches, clamps, or hooks. According to another embodiment, the capillary flow chamber 32 may be permanently affixed to the fixed substrate 16.

Generally, the specimen chamber 34 is provided at the first end of the capillary flow chamber 32 and a fluid absorbing media 36 is provided at the second end of the capillary flow chamber 32. For instance, FIG. 5 illustrates one embodiment wherein the fluid absorbing media 36 is external to the capillary flow chamber 32, and FIG. 6 illustrates a second embodiment wherein the fluid absorbing media 36 is positioned within the capillary flow chamber 32. With respect to the second embodiment as depicted in FIG. 6, the fluid absorbing media 36 is positioned downstream of the avidin coating.

Figure 7:
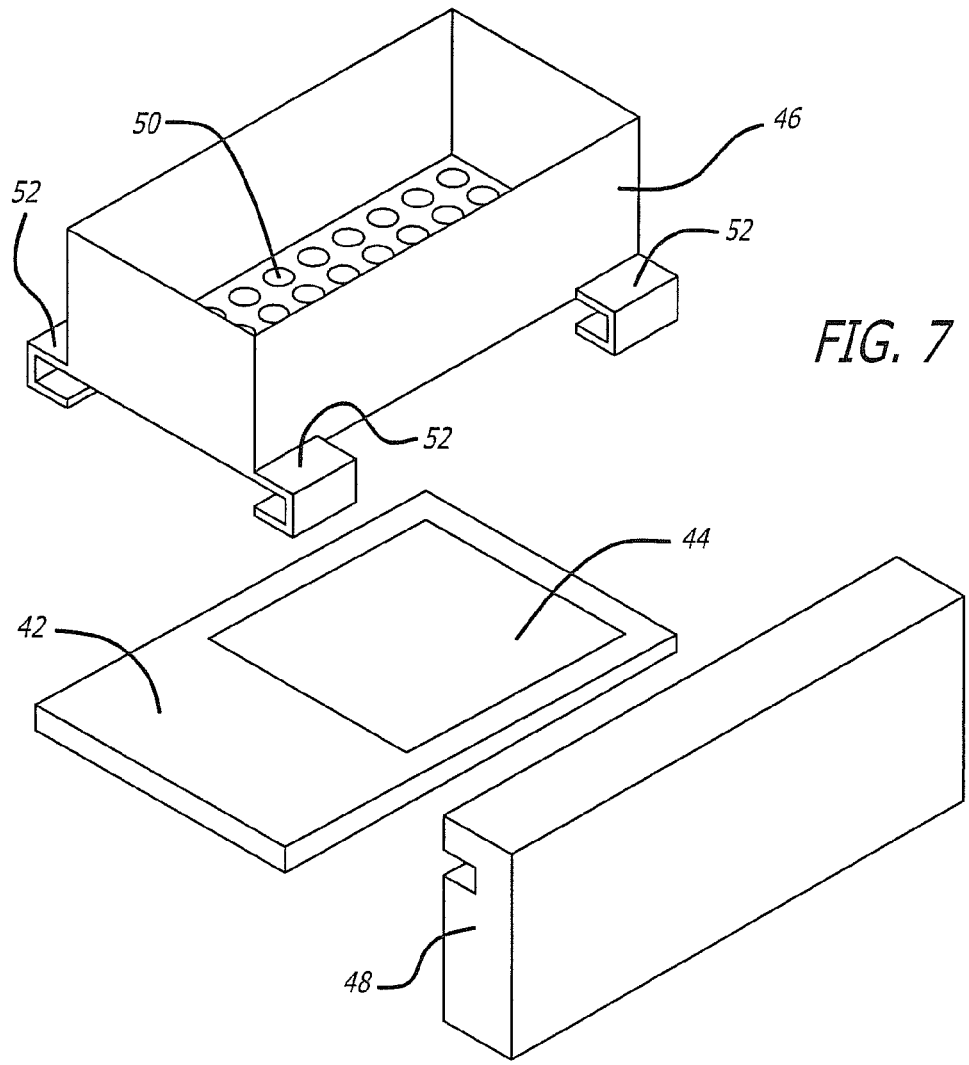
FIG. 7 is a perspective view of another exemplary embodiment of the cell separation device made in accordance with the teachings of the present invention.
Figure 8:
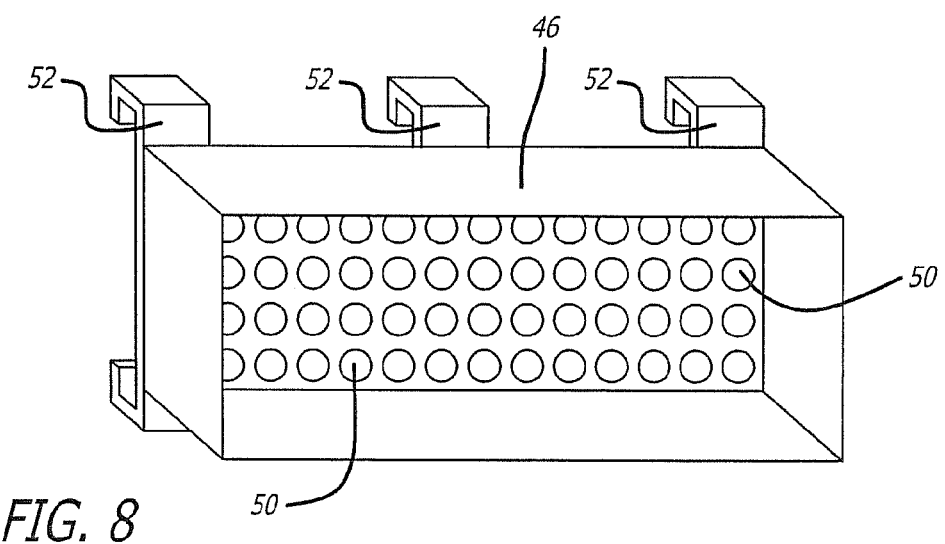
FIG. 8 is a top view of the flow chamber of FIG. 7.

FIGS. 7-8 illustrate another exemplary embodiment of the present invention. The cell separation device 40 comprises a fixed substrate 42 having an avidin coating 44 provided thereon, a flow chamber 46, and a fluid absorbing media 48. Like previous embodiments, the avidin is provided on defined area of the fixed substrate 42. According to one embodiment, the avidin coating comprises a surface area of approximately 8 cm$^2$. Those skilled in the art will appreciate that the surface area may vary in size and is also dependent on the size of the fixed substrate 42.

As shown in FIG. 8, the flow chamber 46 is a housing capable of holding a fluid. According to one exemplary embodiment, the flow chamber 46 may be sized to contain approximately 24 mL of fluids. However, those skilled in the art will appreciate that the capacity of the flow chamber may be varied by altering the size of the flow chamber or the height of the walls. The base of the housing also includes a plurality of holes 50 that allow the cell sample to be delivered onto the avidin coated portion 44 of the fixed substrate 42. Those skilled in the art will appreciate that the size, geometry, and density of holes on the housing base may be varied to alter or optimize fluid flow rates onto the fixed substrate which will also effect target cell capture characteristics of the fixed substrate.

The flow chamber 46 also includes at least one fastening means 52 to attach and detach the flow chamber to the fixed substrate 42. The fastening means may be fasteners such as, but not limited to, braces, latches, clamps, or hooks. According to one embodiment, the fastening means is positioned on the fixed substrate so as to provide clearance distance between the base of the flow chamber and the fixed substrate. Accordingly, like other embodiments of the present invention, this distance is a factor in regulating the flow rate of the cell sample across the avidin coated portion 44 of the fixed substrate 42. Alternatively, the flow chamber 46 may be directly affixed to the surface of the fixed substrate 42. According to this exemplary embodiment, the flow chamber 46 is provided with a skirt (not shown) around the base of the flow chamber. The skirt is also provided with or defines at least one slot (not shown). The slot allows fluid to travel from the avidin portion of the fixed substrate 42 to the fluid absorbing media 48. According to one exemplary embodiment, the flow chamber 46 is provided with one slot that extends along the main axis of the flow chamber as shown in FIG. 7. According to another exemplary embodiment, slots may be positioned on opposing sides of the flow chamber.

As shown in FIG. 7, fluid absorbing media 48 is positioned along one edge of the fixed substrate. However, in alternate embodiments, those skilled in the art will appreciate that fluid absorbing media may be positioned on one or more edges of the fixed substrate to absorb the cell sample solution or washing fluids that may accumulate on the surface of the fixed substrate. The fluid absorbing media 48 is sized so that it may accommodate up to approximately 60 mL of fluid.

In operation, a cell sample is loaded into the specimen chamber. The cell sample flows across the slide, and those cells bound to biotinlyated antibodies are removed from the cell sample as the biotin reacts with the avidin. The binding between the biotin and the avidin is adjustable by varying the flow rate of the cell sample across the avidin coated portion of the fixed substrate. The flow rate may be increased by positioning the capillary flow chamber such that the specimen chamber is above the fluid absorbing media. For instance, the fixed substrate is angled such that the cell sample flows downstream towards the fluid absorbing media. Alternately, the absorptive properties of the fluid absorbing media may be increased or decreased which may increase or decrease the flow of cell sample over the avidin coating. Furthermore, a combination of the absorptive properties of the fluid absorbing media and the incline of the slide may also be adjusted to varying the flow rate of the cell sample across the avidin coated portion of the fixed substrate.

The present invention also relates to methods of isolating specific cells from a mixture of different cells. According to one method of the present invention, the cell preparation is de-bulked of red blood cells using standard laboratory procedures. The preparation is then incubated with a mixture of biotinylated antibodies [$mAb_b$] and fluorescent-conjugated antibodies [$mAb_f$]. The $mAb_b$ and the $mAb_f$ components bind to the target cells in approximate equal proportion. The cell preparation is subsequently washed to remove unbound antibodies and loaded into the specimen-loading chamber of the device. In one embodiment, the loading chamber is designed to accommodate liquid volumes ranging from approximately 5.0 ml to 25.0 ml. The cell preparation then flows through the capillary annulus at a preset flow rate that allows the $mAb_b$ on the target cell surface to bind to the avidin substrate on the slide. Cells that do not bind (non-target cells) are pulled into the absorbent wicking pad by passive absorption.

Washing fluids such as, but not limited to, phosphate buffered saline or water may be then applied into the specimen-loading chamber at a controlled flow rate. This provides for additional movement of unbound cells into the wicking pad. The specimen loading chamber, capillary annulus, and wicking pad may be then removed and the collected target cells may be viewed under a fluorescent microscope. Optionally, the slide may then be fixed with an aldehyde or cell-preservation media for permanence.

According to another exemplary method of the present invention, the cell isolating device may be used to obtain viable target cells. First, the targeted cell is isolated by the preceding methods. After the specimen loading chamber, capillary annulus, and wicking pad are removed from the slide, a second specimen loading chamber and capillary annulus (without a wicking pad) are attached to the slide. Cell releasing agents are loaded into the specimen-loading chamber, and they are allowed to contact the slide. Following a brief incubation time, the chamber is then loaded with a solution (e.g., isotonic buffer, protein medium in solution) that stops the cell releasing chemical reaction. The released target cells are in solution and may be collected in a secondary collection vessel. According to an alternate embodiment, a port may be provided on the annulus/slide interface to allow for the collection of the solution containing the target cells. The cells contained within the secondary collection vessel then may be reacted with other antibodies for subsequent detection and enumeration. According to an alternate method of the present invention, the released cells may be subsequently analyzed by molecular biology techniques for particular cellular genes and/or proteins.

According to one embodiment of the present invention, the cell releasing agent may be a low pH buffer solution having a pH ranging from about 3.0 to 6.0. Examples of the buffer solution that may be adjusted to the desired pH range include, but are not limited to, TRIS (Tris(hydroxymethyl)aminomethane) buffer, phosphate-buffered saline, and lithium carbonate. According to another embodiment, the cell releasing agent may be enzymes such as, but not limited to, chymopapain, trypsin, chymotrypsin, and V8 protease. According to yet another embodiment, the cell releasing agent may be a chemical reagent that cleaves peptide such as, but not limited to, EDTA (Ethylenediaminetetraacetic Acid), cyanogen bromide, or 2-Nitro-5-thiocyanobenzoate.

According to yet another exemplary method of the present invention, viable target cells may be separated from the cell isolating device. First, the targeted cell is isolated by the preceding methods. After the specimen loading chamber, capillary annulus, and wicking pad are removed from the slide, a second specimen loading chamber and capillary annulus (without a wicking pad) are attached to the slide. The second specimen loading chamber is then loaded with an isotonic buffer solution. The isotonic buffer is then allowed to contact the cell isolating device. The buffer solution on the cell isolating device is then mechanically agitated thereby resulting in the breaking of the antigen-antibody bond. As a result, the target cell may be released into the buffer solution and collected for subsequent analysis. According to one exemplary method, the buffer solution may be agitated by sonication or other means of shaking a solution known to those skilled in the art. According to another exemplary method, the cell isolating device may be physically manipulated by sonication or other means to cause the target cells to be separated from the cell isolating device.

In closing, it is to be understood that the embodiments and examples of the present invention are illustrative of the principles of the present invention. Other modifications that may be employed are within the scope of the present invention; thus, by way of example, but not of limitation, alternative configurations and methods of the present invention are also contemplated. Accordingly, the present invention is not limited to that precisely shown and described herein.

What is claimed:

1. A method of recovering a target cell from a cellular mixture comprising:
    exposing a cellular mixture to a targeting solution to form a target cell mixture;
    delivering said target cell mixture through a delivery conduit to a reaction agent pre-applied on a top open planar region of a solid substantially planar reaction surface, said delivery conduit being associated with said solid substantially planar reaction surface;
    controlling the delivery of said target cell mixture by a predetermined delivery distance established between said delivery conduit and said substantially planar reaction surface so as to optimize the flow over said reaction agent pre-applied on said top open planar region of said solid substantially planar reaction surface;
    retaining said target cells on said solid substantially planar reaction surface;
    delivering a releasing solution to said solid substantially planar reaction surface; and
    collecting said releasing solution, wherein said releasing solution includes said target cells.

2. A method of recovering a target cell from a cellular mixture comprising:
    exposing a cellular mixture to a targeting solution to form a target cell mixture;
    delivering said target cell mixture to a reaction substance adhered to a reaction surface from a flow chamber;
    controlling the delivery of said target cell mixture so as to optimize the flow over said reaction substance adhered to said reaction surface;
    retaining said target cells on said reaction surface;
    delivering a releasing solution to said reaction surface; and
    collecting said releasing solution, wherein said releasing solution includes said target cells;
    wherein the controlling of the delivery of the target cell mixture is performed using a device to establish a predetermined delivery distance from said flow chamber for said target cell mixture to traverse to said reaction surface.

3. The method as set forth in claim 2 wherein the predetermined delivery distance is approximately 2 to 20 microns.

4. The method as set forth in claim 2, wherein controlling the delivery of the target cell mixture further includes absorbing non-reacting amounts of said target cell solution from said reaction surface at an optimized rate.

5. The method of claim 4 further comprising delivering another aliquot of the target cell releasing solution to said reaction surface, mechanically agitating said target cell releasing solution, and collecting said target cell releasing solution, wherein said target cell releasing solution includes said target cells.

6. The method of claim 2 wherein said targeting solution includes a marker compound comprising a binder molecule and a probe.

7. The method of claim 6 wherein said probe is selected from the group consisting of flurochromes, radiolabels, fluorescent agents, and chromophores.

8. The method of claim 2 wherein said reaction surface comprises a bioactive coating selected from the group consisting of avidin, streptavidin, avidin derivatives, streptavidin derivatives, and blends thereof.

9. The method of claim 2 wherein said releasing solution is a buffer solution having a pH ranging from about 3.0 to 6.0.

10. The method of claim 2 wherein said releasing solution includes a cell releasing agent selected from the group consisting of chymopapain, trypsin, chymotrypsin, V8 protease, Ethylenediaminetetraacetic Acid, cyanogen bromide, and 2-Nitro-5-thiocyanobenzoate.

11. The method as set forth in claim 1, wherein the predetermined delivery distance is approximately 2 to 20 microns.

12. The method as set forth in claim 1, wherein controlling the delivery of the target cell mixture further includes absorbing non-reacting amounts of said target cell solution from said reaction surface at an optimized rate.

13. The method of claim 12 further comprising delivering another aliquot of the target cell releasing solution to said reaction surface, mechanically agitating said target cell releasing solution, and collecting said target cell releasing solution, wherein said target cell releasing solution includes said target cells.

14. The method of claim 1 wherein said targeting solution includes a marker compound comprising a binder molecule and a probe.

15. The method of claim 14 wherein said probe is selected from the group consisting of flurochromes, radiolabels, fluorescent agents, and chromophores.

16. The method of claim 1 wherein said reaction surface comprises a bioactive coating selected from the group consisting of avidin, streptavidin, avidin derivatives, streptavidin derivatives, and blends thereof.

17. The method of claim 1 wherein said releasing solution is a buffer solution having a pH ranging from about 3.0 to 6.0.

18. The method of claim 1 wherein said releasing solution includes a cell releasing agent selected from the group consisting of chymopapain, trypsin, chymotrypsin, V8 protease, Ethylenediaminetetraacetic Acid, cyanogen bromide, and 2-Nitro-5-thiocyanobenzoate.

19. The method of claim 1, further comprising optionally analyzing said target cells on said planar reaction surface after the retaining of said target cells on said solid substantially planar reaction surface and prior to the delivering of a releasing agent to said solid substantially planar reaction surface.

20. The method of claim 2, further comprising optionally analyzing said target cells on said reaction surface after the retaining of said target cells on said reaction surface and prior to the delivering of a releasing agent to said reaction surface.

21. The method of claim 1, further comprising analyzing said target cells on said planar reaction surface after the retaining of said target cells on said solid substantially planar reaction surface and prior to the delivering of a releasing agent to said solid substantially planar reaction surface.

22. The method of claim 2, further comprising analyzing said target cells on said reaction surface after the retaining of said target cells on said reaction surface and prior to the delivering of a releasing agent to said reaction surface.

23. The method of claim 21, wherein the analyzing of said target cells includes identifying said target cells.

24. The method of claim 22, wherein the analyzing of said target cells includes identifying said target cells.

25. The method of claim 1, wherein the delivering of said target cell mixture to a solid substantially planar reaction surface includes delivering said target cell mixture to a reaction surface on a slide suited for viewing through a microscope.

26. The method of claim 2, wherein the delivering of said target cell mixture to a reaction surface includes delivering said target cell mixture to a reaction surface on a slide suited for viewing through a microscope.

27. The method of claim 2, wherein the device establishing said predetermined delivery distance is the flow chamber.

\* \* \* \* \*